United States Patent [19]

Prange et al.

[11] 4,156,785

[45] May 29, 1979

[54] METHOD OF PREPARING α,β-UNSATURATED CARBOXYLIC ACID ESTERS

[75] Inventors: Uwe Prange, Niederkassel; Hermann Richtzenhain, Much-Schwellenbach; Wilhelm Vogt, Cologne-Sülz, all of Fed. Rep. of Germany

[73] Assignee: Dynamit Nobel Aktiengesellschaft, Cologne, Fed. Rep. of Germany

[21] Appl. No.: 599,913

[22] Filed: Jul. 28, 1975

[30] Foreign Application Priority Data

Jul. 31, 1974 [DE] Fed. Rep. of Germany ....... 2436788

[51] Int. Cl.² .............................................. C07C 09/56
[52] U.S. Cl. .................................... 560/206; 560/104; 560/114
[58] Field of Search ................. 260/486 AC; 560/206, 560/104, 114

[56] References Cited

U.S. PATENT DOCUMENTS

| | | | |
|---|---|---|---|
| 3,116,306 | 12/1963 | Heck | 260/476 R |
| 3,974,202 | 8/1976 | El-Chahewi et al. | 260/476 R |

OTHER PUBLICATIONS

J. Falbe, Carbon Monoxide in Organic Synthesis, pp. 78–100.
Von Gian Paolo Chiusoli et al., Zeitschrift für Naturforschung, vol. 176, 1962.
Heck, P. F. et al., JACS, 85, 2779–2782 (1963).
Cotton et al., Adv. Inorg. Chem., 3rd Ed., pp. 702–703 (1972).
Sidgwick, Chem. Elem. and Their Compounds, vol. II, p. 1422 (1950).

*Primary Examiner*—Paul J. Killos
*Attorney, Agent, or Firm*—Sprung, Felfe, Horn, Lynch & Kramer

[57] ABSTRACT

Process of preparing an α,β-unsaturated carboxylic acid ester, comprising contacting an α,β-unsaturated halogen compound with carbon monoxide, an alkali alcoholate in the presence of a metal carbonyl as catalyst, in an alcohol that is the basis of the alkali alcoholate, at a pH of 8.5–11.5. Thereby, for example, crotonic acid methyl ester can be produced from allyl chloride.

12 Claims, 1 Drawing Figure

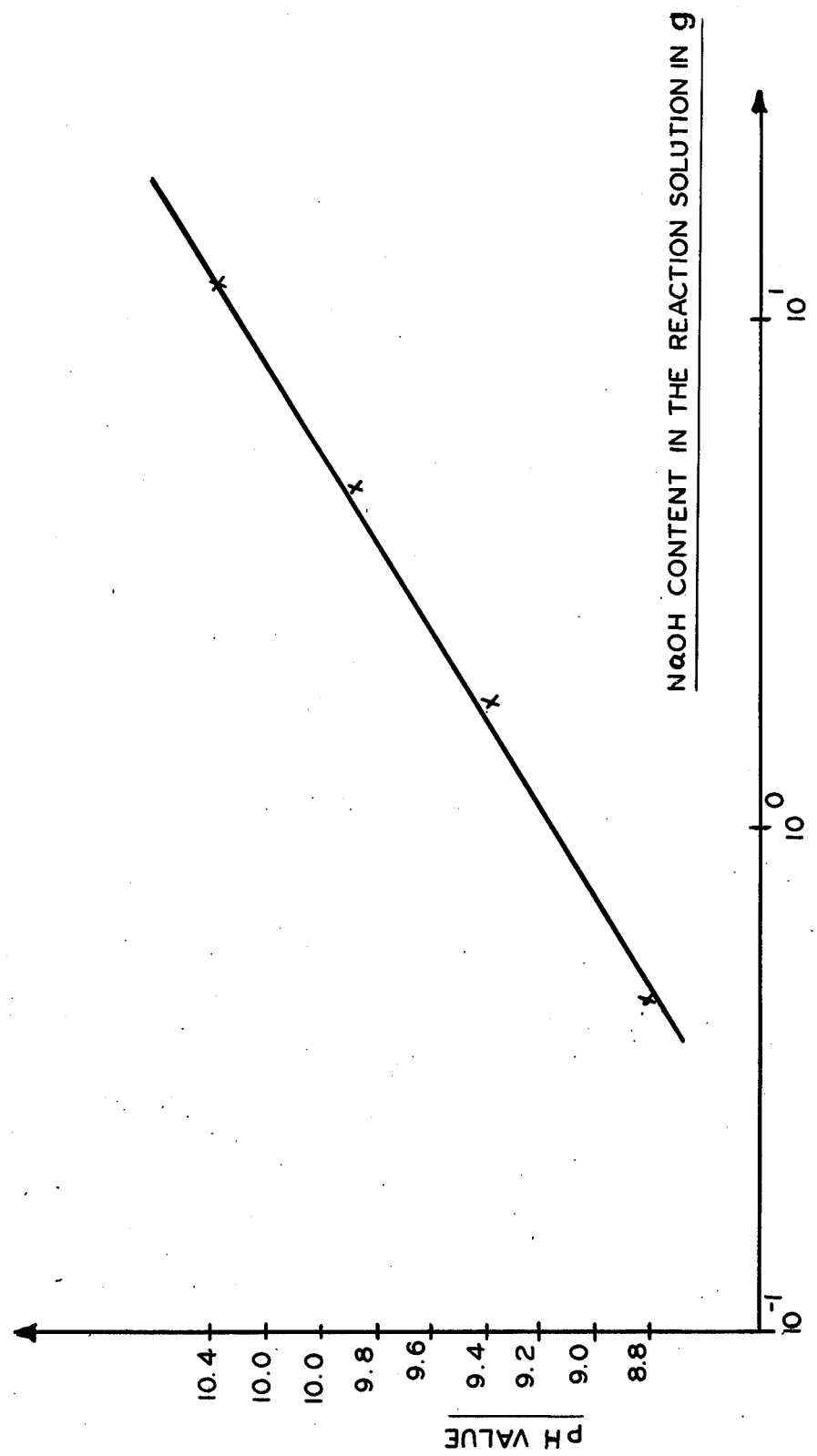

METHOD OF PREPARING α,β-UNSATURATED CARBOXYLIC ACID ESTERS

BACKGROUND

The present invention relates to a method of preparing α,β-unsaturated carboxylic acid esters by the reaction of α,β-unsaturated halogen compounds with carbon monoxide and alkali alcoholates in the present of alcohols and catalysts.

Setting out from α,β-unsaturated halides, known reactions are used to produce predominantly vinyl acetic acid esters or their homologs, such as β,γ-carboxylic acid esters, that is, those in which the position of the halide is the same as it was in the halide, while α,β-unsaturated carboxylic acid esters, in which the position of the double bond is shifted one position in the chain, form not at all or only in small amounts as by-products.

Thus it is known that crotonic acid methyl ester in small amounts plus vinyl acetic acid methyl ester are formed from allyl chloride with carbon monoxide and methanol in the presence of catalytic amounts of nickel carbonyl and thiourea at atmospheric pressure and at a temperature between 15° and 35° C. at a pH between 5.5 and 9. Vinyl acetic acid methyl ester, however, can be transformed to crotonic acid methyl ester only with great difficulty, for example by heating with 10 wt.-% of basic ion exchanger at 100° C. for 10 hours to produce a yield of up to 70%, or by treatment with 2% methanolic NaOH at room temperature, although approximately 30% of 2-methoxybutyric acid methyl ester is produced (German "Offenlegungsschrift" No. 1,936,725).

It is furthermore known that palladium salts catalyze the carbonylation of allyl chloride at approximately 100 atmospheres of carbon monoxide pressure. In the presence of an inert solvent such as benzene, vinyl acetyl chloride forms; in an alcohol as solvent, the corresponding vinyl acetic acid esters form. Crotonic acid chloride or crotonic acid esters are produced only as by-products by the isomerization of the double bond (J. Tsuji, J. Kiji, S. Imamura and M. Morikawa, J.Amer.Chem.Soc., 86, 4350 (1964) and D. Medema, R. van Helden and C. F. Kohll, Inorg. Chim. Acta, 3, 255 (1969).

Disadvantages of both these processes lie in the fact that the preparation of the carboxylic acid esters must be performed in two steps, that only part of the vinyl acetic ester is reacted to crotonic acid esters, that in the one case the reaction times are too long, and in the other case very appreciable amounts of by-products are formed.

Another approach to the manufacture of crotonic acid esters consists in the oxidation of crotonic aldehyde to crotonic acid (Ullmann 1960, vol. 5, p. 617), followed by esterification (Jeffery and Vogel, J.Chem.Soc. 1948, 666). Here, again, two process steps are required, and the yields are about 80%.

THE INVENTION

It has now been found that the preparation of α,β-unsaturated carboxylic acids can be performed in a one-step process by the reaction of α,β-unsaturated halogen compounds with carbon monoxide in an alcohol, in the presence of an alkali alcoholate that is the basis of the alcohol, and of catalytic amounts of metal carbonyl.

The subject matter of the invention is a process for the preparation of α,β-unsaturated carboxylic acid esters which is characterized in that an α,β-unsaturated halogen compound is reacted in an alcohol with an alkali alcoholate of the same alcohol, plus carbon monoxide, in the presence of catalytic amounts of a metal carbonyl in a pH range of 8.5 to 11.5, preferably 8.8 to 10.5.

The reaction takes place according to the equation:

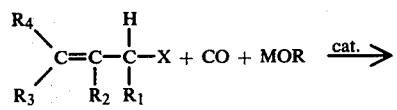

I.

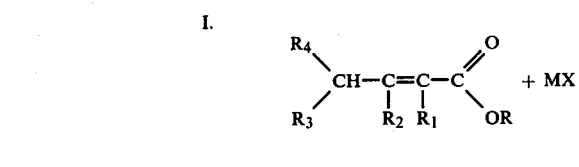

II.

In this reaction equation, $R_1$, $R_2$, $R_3$ and $R_4$ can represent a hydrogen atom, an alkyl, cycloalkyl, aryl or aryl-substituted alkyl radical of 1 to 20 carbon atoms, the alkyl radicals being preferably straight-chained or branched and having 1 to 4 carbon atoms, the cycloalkyl radicals being preferably those having 5 to 8 carbon atoms, and the aryl radicals being preferably mononuclear radicals, especially the phenyl radical. $R_1$ and $R_3$ or $R_4$ can also together be a component of a cycloalkane having 3 to 20 carbon atoms, preferably having 5 to 7 carbon atoms. X represents the halogens chlorine, and in some cases bromine or iodine, and M represents an alkali metal, preferably sodium or potassium. The radical R of the ester is generally straight-chained or branched, preferably saturated, alkyl radicals having 1 to 20 carbon atoms, preferably the radicals of the alcohols named below having 1 to 8 carbon atoms, and in some cases an alkoxy substituent.

Important advantages of the invention are that

1. The α,β-unsaturated carboxylic acids can be prepared in a single reaction step from α,β-unsaturated halogen compounds,
2. No addition of thiourea to the $Ni(CO)_4$ is necessary, so that bad odors caused by sulfurous compounds in the product are avoided,
3. A large number of α,β-unsaturated halogen compounds, alcohols and alcoholates can be used, and
4. High yields of α,β-unsaturated carboxylic acid esters can be achieved.

The reaction is performed by adding alkali alcoholate solution and the α,β-unsaturated halogen compound drop by drop to an alcoholic solution of the metal carbonyl such that, on the basis of the $H_2O$ content of the alcohol and the alkali hydroxide content of the alkali alcoholate, a pH of 8.5 to 11.5 is maintained. It has been found experimentally that the maximum yield of α,β-unsaturated carboxylic acid esters depends on the $H_2O$ concentration in the alcohol or the alkali concentration in the alcoholate, as the case may be. If the logarithm of the $H_2O$ concentration and alkali concentration, respectively, is plotted against the pH value of the reaction solution, a straight line is obtained which rises towards increasing pH values as the alkali hydroxide content or water content of the reaction solution, as the case may be, increases (cf. FIG. 1).

Suitable α,β-unsaturated halogen compounds are, for example, allyl chloride, crotyl chloride, 1-methallyl chloride, 2-methallyl chloride, 1-chloropentene-2, 1-chlorohexene-2 and higher α,β-unsaturated halogen compounds having up to 20 carbon atoms, but also cyclic compounds such as 1-bromocyclohexene-2.

Preferred alcohols are the univalent alcohols, which can be straight-chained or branched, and can in some cases have an alkoxy substituent having 1 to 4 carbon atoms, examples being methanol, ethanol, propanol, isopropanol, n-butanol, isobutanol, sec.-butanol, tert.-butanol, pentanol, 2-ethylhexanol, cyclohexanol, methyl glycol or ethyl glycol.

For 1 mole of α,β-unsaturated halogen compound at least 1 mole of alkali alcoholate is desirable, but a slight excess of about 5 to 10% is better so as to assure a pH between 8.5 and 11.5 at the end of the reaction. The alkali alcoholates are the sodium and potassium alcoholates of the above-described alcohols, and they are added preferably after being dissolved in the alcohol in question.

The reaction of the above-mentioned materials is performed in the temperature range from 0° to 100° C., preferably between 20° and 80° C. The reaction time amounts to from 1 to 10 hours depending on the temperature and the amount of catalyst.

The reaction of the α,β-unsaturated halogen compounds takes place at a pressure between 0.5 at. and 5 at., preferably betwen 1.0 at. and 4.0 at. Higher pressures are possible, but not necessary.

The catalysts can be $Ni(CO)_4$, $Co_2(CO)_8$, or those nickel-containing compounds which react with carbon monoxide under the conditions of the reaction to form $Ni(CO)_4$. The molar ratio of catalyst to allyl halide can be between 1:10 and 1:500, but will preferably be between 1:15 and 1:200.

The α,β-unsaturated carboxylic acid esters prepared in this manner, such as crotonic acid esters for example, are suitable for the preparation of polymers and of copolymers with vinyl acetate, acrylate, methacrylate and vinyl chloride and other substances. They are suitable as solvents and plasticizers and as intermediates for the preparation of β-substituted butyric acid esters and glutaric acid derivatives. Some esters find use as pesticides, fungicides and herbicides, an example being the herbicide "Karathane" ((2,4-dinitro-1-methylheptyl)-phenylcrotonate). To form maximal yields of α,β unsaturated carboxilic acid esters it has been appropriate to add a small amount of water to the reaction mixture or, which measure is equivalent, to add a small amount of NaOH resp. to use an alcoholate containing such small amounts of alkali hydroxide.

The amount may be from 0.01 to about 5.0 wt.% NaOH in the reaction mixture, but every pH is correlated to a certain content of NaOH (or added water) or certain values around an optimal content resulting maximal conversation to α,β-unsaturated acidesters and optimal yields of desired product. This more closely may be seen from example 2 and especially from FIG. 1 on attached drawing.

Though this effect is not fully understood we found that at low pH of say 9 a low NaOH content and at high pH of say 10 or 10.5 higher NaOH contents will result best conditions for most specifical conversation into α,β-unsaturated acid esters. Having constant NaOH concentration a low pH will rise the amount of vinylacetic acid ester while high pH will rise the amount of β-alkoxy substituted acid esters, both being undesired.

EXAMPLES

EXAMPLE 1

Three ml of $Ni(CO)_4$ in 200 ml of $CH_3OH$ containing 0.4 wt.-% of $H_2O$ are placed in a reaction vessel of 1 liter capacity, equipped with a stirrer, 2 dropping funnels, a condenser and a gas feed tube. For the measurement of the pH value, the vessel is provided with a glass electrode in the form of a single-rod electrode with 3.5x molar aqueous KCl solution as the conductive salt solution. The vessel is flooded with carbon monoxide and a pressure of 1.8 at. is established. At a temperature of 60° C., a pH of 9.9 is established with a few drops of sodium methylate. Then, with strong stirring, 76.5 g (1 mole) of allyl chloride with 100 ml of $CH_3OH$ is added drop by drop over a period of one hour, while at the same time 270 g of 20 wt.-% sodium methylate solution in methanol containing 0.9 wt.-% NaOH is fed in from another proportioning system such that the pH varies by no more than 0.2 units. Carbon monoxide is proportioned during the reaction such that a pressure of 1.8 atmospheres is maintained. When the addition of the components has ended, stirring is continued for 1 hour at 60° C. and pH 9.9, and then the mixture is let cool to room temperature and acidified with a small amount of $H_2SO_4$. The precipitated inorganic salt is removed by filtration and the reaction solution is distilled. The distillation yields 86 g of crotonic acid methyl ester (90% yield) at a transformation of 95.5% of the allyl chloride, a small amount of the crotonic acid methyl ester being in the form of the cis isomer; also, 2.7 g of vinyl acetic acid methyl ester (3% yield) and 6 g of β-methoxybutyric acid methyl ester (5% yield).

EXAMPLE 2

Under the conditions described in Example 1, but with varying amounts of $H_2O$ on the methanol and of NaOH in the sodium methylate, and hence different pH values, the results listed in Table 1 are obtained after processing:

Table 1

| | | | | |
|---|---|---|---|---|
| NaOH content in the Reaction Solution in g | 0.45 | 1.70 | 4.50 | 11.3 |
| pH value | 8.8 | 9.4 | 9.9 | 10.4 |
| Allyl chloride transformation | 100% | 100% | 95.5% | 100% |
| Yield of: | | | | |
| Crotonic acid methyl ester | 89.0% | 90.0% | 90.0% | 89.2% |
| Vinyl acetic acid methyl ester | 4.5% | 3.9% | 3.0% | 2.4% |
| β-methoxybutyric acid methyl ester | 6.0% | 4.0% | 5.0% | 7.4% |

EXAMPLE 3

Same as Example 1, but with the use of 1.1 mole of sodium ethylate in the form of a solution of 14.5% by weight in ethanol with a content of 0.62 wt.-% of NaOH, and 200 ml of ethanol containing 0.28 wt.-% of $H_2O$, one mole of allyl chloride is reacted at 1.5 at. and a pH of 10.0. The filtration and distillation yield 94.0 g of crotonic acid ethyl ester (yield 89.5%, 6.9 g of vinyl acetic acid ethyl ester (yield 6.6%) and 0.7 g of β-ethoxybutyric acid ethyl ester (yield 0.5%) for a transformation of 92.4% of the allyl chloride.

EXAMPLE 4

76.5 g of allyl chloride is reacted as in Example 1, but instead of sodium methylate and methanol 1.1 moles of a 20 wt.-% sodium-n-butylate solution in n-butanol containing 0.4 wt.-% of NaOH are used, and n-butanol containing 0.18 wt.-% of $H_2O$. The conventional performance of the reaction at pH 9.9, 1.2 atmospheres CO pressure and 60° C. results in a transformation of 87.6% of the allyl chloride. 110 g of crotonic acid-n-butyl ester is obtained (yield 88.5%) plus 3 g of vinyl acetic acid n-butyl ester (yield 2.4%) and 8.5 g of β-n-butoxybutyric acid n-butyl ester (yield 4.3%).

EXAMPLE 5

38.3 g (0.5 mole) of allyl chloride is reacted under the conditions described in Example 1, at 60° C., 1.2 atmospheres of CO pressure, and in the presence of 2 ml of $Ni(CO)_4$, with 0.54 mole of sodium isopropylate in the form of an 8.5 wt.-% solution in isopropanol containing 0.89 wt.-% NaOH, in 200 g of isopropanol containing 0.4 wt.-% of $H_2O$, at a pH of 10.2. The sodium isopropylate is maintained at about 60° C. to prevent the formation of crystals. After the distillation, 35.6 g of crotonic acid isopropyl ester (yield 83%) and 3.1 g of vinyl acetic acid isopropyl ester (yield 7.2%) are obtained, at a Cl transformation of 67.6% according to gas chromatogram (Hewlett-Packard, DC 200 silicone oil column, length 4 m).

EXAMPLE 6

76.5 g (1 mole) of allyl chloride is reacted as in Example 1, at 60° C., 1.8 atmospheres of CO pressure, and a pH of 10.2, in the presence of 5 ml of $Ni(CO)_4$, but in 200 g of methyl glycol containing 0.16 wt.-% of $H_2O$, with 1.1 moles of sodium methyl glycolate in a 28.5 wt.-% solution in methyl glycol containing 0.35 wt.-% of NaOH, over a period of 4 hours. At a Cl' transformation of 84.2%, 91 g of crotonic acid-2-methoxyethylester (yield 75%) and 19.5 g of vinyl acetic acid-2-methoxy-ethylester (yield 16%) are obtained by gas chromatography (Hewlett-Packard, DC 200 silicone oil column, length 4 m).

EXAMPLE 7

In a manner similar to Example 1, 76.5 g of allyl chloride is reacted over a period of 4 hours, in the presence of 5 ml of $Ni(CO)_4$, at 1.2 at. CO pressure and at a pH of 10.0, at 60° C., in 200 grams of ethyl glycol containing 0.14 wt.-% of $H_2O$, with 1.12 moles of 20.4% sodium ethyl glycolate in ethyl glycol containing 0.31 wt.-% of NaOH. The distillate contains, according to gas chromatographic analysis (Hewlett-Packard, DC 200 silicone oil, length 4 m), 105 g of crotonic acid-2-ethoxyethylester (yield 80%) and 16 g of vinyl acetic acid-2-ethoxyethylester (yield 12%).

EXAMPLE 8

Similar to Example 1, except that 76.5 g of allyl chloride is reacted over a period of 6 hours at 40° C., at a CO pressure of 1 at., and in the presence of 2 ml of $Ni(CO)_4$, with 1.12 moles of sodium methylate as a 20 wt.-% methanolic solution, and carbon monoxide. 92 g of crotonic acid methyl ester (yield 92%) and 8.6 g of β-methoxybutyric acid methyl ester (yield 6.5%) are isolated, at a transformation of 100%.

EXAMPLE 9

90.6 g (1 mole) of methallyl chloride is reacted under the conditions described in Example 1, at 60° C., 1.8 at. CO pressure, pH 10.2, in the presence of 5 ml of $Ni(CO)_4$ and 200 ml of methanol containing 0.4 wt.-% of $H_2O$, with 1.05 moles of sodium methylate as a 20.4 wt.-% methanolic solution containing 0.9 wt.-% of NaOH. After acidification with $H_2SO_4$ distillation is performed. The distillate, at a Cl' transformation of 89.4%, contains, according to gas chromatographic analysis (Hewlett-Packard, DC 200 silicone oil column, 4 m), 93 g of β,β-dimethylacrylic acid methyl ester (yield 91%) and 2.3 g of 3-methylbutene-3-acid methyl ester (yield 2.2%).

EXAMPLE 10

90.6 g (1 mole) of trans-crotyl chloride is reacted as in Example 9. At a Cl' transformation of 92.2%, 87.4 g of pentene-2-acid methyl ester (yield 82.5%) and 17 g of β-methoxyvaleric acid methyl ester (yield 12.5%) are obtained according to gas chromatogram.

EXAMPLE 11

In a manner similar to Example 1, 38.3 g of allyl chloride is reacted with sodium methylate and carbon monoxide in the presence of 10 g of $Co_2(CO)_8$ instead of the $Ni(CO)_4$ specified in Example 1. At a transformation of 73.6%, 26.7 g of crotonic acid methyl ester (yield 72.5%) and 4.3 g of β-methoxybutyric acid methyl ester (yield 8.9%) are isolated.

What is claimed is:

1. Process of preparing an α,β-unsaturated carboxylic acid ester, comprising contacting an α,β-unsaturated halogen compound with carbon monoxide, an alkali alcoholate and in the presence of a catalystic amount of nickel or cobalt carbonyl in an alcohol that is the basis of the alkali alcoholate in a pH range between 8.5 and 11.5, at a temperature and for a time sufficient for the reaction of said α,β-unsaturated halogen compound to form said α,β-unsaturated carboxylic acid ester.

2. Process of claim 1, wherein said metal carbonyl and α,β-unsaturated halogen compound are present in the molar ratio of 1:10 to 1:500.

3. Process of claim 1, wherein said alcohol is a primary, secondary or tertiary univalent alcohol having 1 to 20 carbon atoms.

4. Process of claim 1, wherein said alcoholate is sodium or potassium alcoholate.

5. Process of claim 1, wherein the temperature is 0°–100° C.

6. Process of claim 1, wherein the contacting is performed at a carbon monoxide pressure of 0.5 to 5 atmospheres.

7. Process of claim 1 wherein said α,β-unsaturated halogen compound is an allyl halide of the formula:

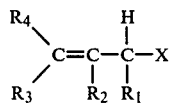

and said α,β-unsaturated carboxylic acid ester is of the formula

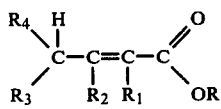

$R_1$, $R_2$, $R_3$ and $R_4$ is each hydrogen, alkyl, cycloalkyl, aryl, or aryl-substituted alkyl radical having 1 to 20 carbon atoms, with the proviso that $R_1$ and $R_3$ or $R_4$ may represent a component of cycloalkyl having 3 to 20 carbon atoms;

X is chlorine, bromine, or iodine; and

R is straight chained or branched alkyl having 1 to 20 carbon atoms.

8. Process of claim 7, wherein the catalyst is a nickel or cobalt carbonyl, said metal carbonyl and α,β-unsaturated halogen compound are present in the molar ratio of 1:10 to 1:50, said alcohol is a primary, secondary or tertiary univalent alcohol having 1 to 20 carbon atoms, said alcoholate is sodium or potassium alcoholate, the temperature zone is 0°–100° C., and the contacting is performed at a carbon monoxide pressure of 0.5 to 5 atmospheres.

9. Process of claim 1, wherein water or alkali hydroxide is present during said contacting.

10. Process of claim 1, wherein alkali hydroxide in amount of 0.01 to 5.0 wt.% is present during said contacting.

11. Process of claim 1, wherein said contacting is in the presence of a catalytic amount of nickel carbonyl.

12. Process of claim 1, wherein said contacting is in the presence of a catalytic amount of cobalt carbonyl.

* * * * *

UNITED STATES PATENT AND TRADEMARK OFFICE
CERTIFICATE OF CORRECTION

PATENT NO. : 4,156,785
DATED : May 29, 1979
INVENTOR(S) : Uwe Prange et al.

It is certified that error appears in the above-identified patent and that said Letters Patent are hereby corrected as shown below:

Colum 6, line 39, (Claim 1, line 4), change

"catalystic" to -- catalytic --.

Signed and Sealed this

Twenty-ninth Day of July 1980

[SEAL]

Attest:

SIDNEY A. DIAMOND

Attesting Officer  Commissioner of Patents and Trademarks